United States Patent
Prudencio Pignatelli et al.

(10) Patent No.: US 9,655,957 B2
(45) Date of Patent: May 23, 2017

(54) **RODENT *PLASMODIUM* PARASITES AS PLATFORMS FOR A WHOLE-ORGANISM MALARIA VACCINE**

(71) Applicant: INSTITUTO DE MEDICINA MOLECULAR, Lisbon (PT)

(72) Inventors: Rui Miguel Prudencio Pignatelli, Lisbon (PT); Maria Manuel Dias Da Mota, Lisbon (PT); Antonio Manuel Barbeiro Mendes, Leiria (PT)

(73) Assignee: INSTITUTO DE MEDICINA MOLECULAR, Lisbon (PT)

( * ) Notice: Subject to any disclaimer, the term of this patent is extended or adjusted under 35 U.S.C. 154(b) by 0 days.

(21) Appl. No.: 14/394,964

(22) PCT Filed: Apr. 17, 2013

(86) PCT No.: PCT/IB2013/053050
§ 371 (c)(1),
(2) Date: Oct. 16, 2014

(87) PCT Pub. No.: WO2013/156949
PCT Pub. Date: Oct. 24, 2013

(65) Prior Publication Data
US 2015/0071966 A1    Mar. 12, 2015

(30) Foreign Application Priority Data
Apr. 17, 2012 (PT) .................................. 106262

(51) Int. Cl.
*A61K 39/015* (2006.01)
*A61K 39/00* (2006.01)

(52) U.S. Cl.
CPC ........ *A61K 39/015* (2013.01); *A61K 2039/52* (2013.01); *A61K 2039/523* (2013.01); *A61K 2039/58* (2013.01)

(58) Field of Classification Search
None
See application file for complete search history.

(56) References Cited

PUBLICATIONS

Mueller et al (Nature 433(7022):164-167, 2005).*
Dunachie et al PLoS One, 5(9):e12557, 2010.*
Radosevic et al (Clinical and Vaccine Immunology 17(11):1687-1694, 2010).*
Aide et al PLoS One, 5(11):e13828.*
Playfair et al (Immunology 33:507-515, 1977).*

* cited by examiner

*Primary Examiner* — Patricia Duffy
(74) *Attorney, Agent, or Firm* — Sughrue Mion, PLLC

(57) ABSTRACT

A method for inducing protective immunity in a vertebrate host against malaria, by administering to the host a live rodent *Plasmodium* organism and exploiting its cross-species protection potential.

Figure 1:
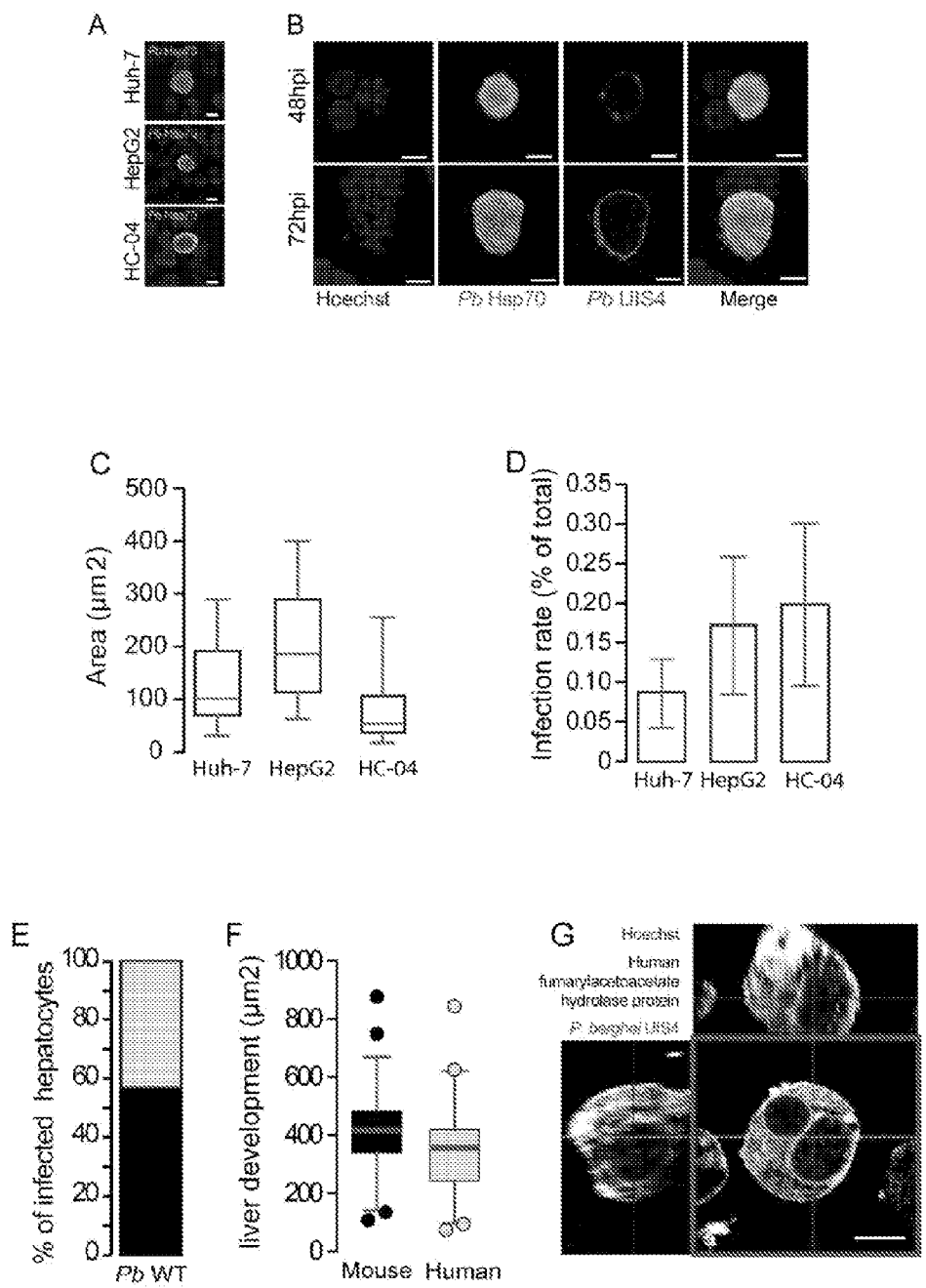

A method to use genetically engineered live rodent *Plasmodium* organisms expressing antigens from different stages of the life cycle of human-infective *Plasmodium* species to immunize vertebrate hosts against malaria.

The invention further provides for the production of a vaccine composition, by suspending wild-type or genetically modified rodent *Plasmodium* organisms in a suitable pharmaceutically acceptable carrier solution.

8 Claims, 6 Drawing Sheets

E

Light microscopy

Immunofluorescence microscopy
(DAPI: nuclei)

Immunofluorescence microscopy
(TER-119: rodent erythrocytes)

RODENT *PLASMODIUM* PARASITES AS PLATFORMS FOR A WHOLE-ORGANISM MALARIA VACCINE

CROSS REFERENCE TO RELATED APPLICATIONS

This application is a National Stage of International Application No. PCT/IB2013/053050 filed Apr. 17, 2013, claiming priority based on Portuguese Patent Application No. 106262 filed Apr. 17, 2012, the contents of all of which are incorporated herein by reference in their entirety.

FIELD OF THE INVENTION

This invention provides a method for inoculating a vertebrate host against malaria by administering to the host a live rodent *Plasmodium* organism and exploiting its cross-species protection potential. The invention further provides a vaccine composition comprising a rodent *Plasmodium* organism that is genetically engineered to express immunospecific single (liver, blood or gametocyte) or multi (liver and blood, or liver and gametocyte, or blood and gametocyte, or liver and blood and gametocyte) stage immuneeffectors from one or several human *Plasmodium* parasites. The invention also provides for production of a vaccine composition, by suspending wild-type or genetically modified rodent *Plasmodium* organisms in a suitable pharmaceutically acceptable carrier solution.

BACKGROUND OF THE INVENTION

The long-standing goal of an effective vaccine against malaria constitutes a crucial component of efforts to eradicate a disease that, according to recent estimates, kills over 1 million persons per year. Malaria vaccines can target sexual and mosquito stage parasite antigens, pre-erythrocytic vaccines that reduce asexual and sexual stage parasite burdens, asexual erythrocytic stage vaccines that reduce blood-stage parasite densities, and vaccines that disrupt parasite development in the vector. So far, vaccines against the early pre-erythrocytic stages have shown most success among current vaccine candidates [1], including the circumsporozoite (CS) protein-based leading vaccine candidate, RTS,S. However, recent results of a phase 3 trial of this subunit vaccine have revealed only modest efficacy of protection against severe malaria [2].

An alternative to subunit vaccine candidates is the use of a whole-organism approach. Such a strategy is based on the generation of immunity by attenuated sporozoites, the *Plasmodium* form that is injected by an infected mosquito into its vertebrate host. During a natural malaria infection, an asymptomatic parasite maturation and extensive replication phase inside hepatocytes leads to the generation of *Plasmodium* exoerythrocytic forms (EEFs) and precedes the release of erythrocyte-infectious merozoites that cause disease (reviewed in [3]). A few decades ago, it was shown that sterile protection of humans could be achieved through the injection *P. falciparum* radiation-attenuated sporozoites (RAS) [4]. More recently, it was shown that sporozoites deficient in certain genes, and which become impaired in complete *Plasmodium* development inside the liver hepatocyte (GAS), can confer long-lasting protection against malaria in rodents [5]. This has created renewed hopes for a whole-organism vaccine against malaria based on genetically attenuated *Plasmodium* sporozoites (GAS). Both RAS and GAS are able to invade hepatocytes but fail to complete their developmental process in the liver. Importantly, late liver stage-arresting parasites seem to trigger antimalarial immunity superior to early-arresting variants [6], although they might increase the risk of breakthrough infections.

The protective efficacy of RAS and GAS involves conserved mechanisms and seems to be mainly mediated through the activity of induced $CD8^+$ T cells, although antibodies also contribute to protection. *Plasmodium* CS is the immunodominant protective antigen in both RAS and GAS [7] and previous studies have shown that protection could be achieved by immunization with CS alone. However, it is also clear that CS is not the sole immunogen at play in the immunity triggered by a whole-organism approach [8, 9].

One major potential drawback of current pre-erythrocytic whole-organism malaria vaccination strategies is that they rely on the attenuation of *P. falciparum*, the deadliest human-infective parasite species. It has been shown that the radiation dose required to generate effective RAS must be finely tuned to meet minimal requirements. Indeed, sporozoites exposed to high radiation levels will not induce protection, while parasites exposed to low levels will induce breakthrough infection. Similarly to latter, breakthrough infections with different GAS have been reported [10]. Since a single sporozoite undergoing complete development in the liver can give rise to blood infection and malaria symptoms, a vaccination based on the attenuation of *P. falciparum* sporozoites poses safety concerns that cannot be ignored.

In this context, we hereby propose an alternative strategy for the development of a pre-erythrocytic, whole-organism vaccine against malaria, based on the use of rodent *Plasmodium* parasites as a non-pathogenic vector of human immunization. Here, we demonstrate that *P. berghei* is capable of infecting human hepatocytes, as required for optimal antigen presentation, while being unable to cause a blood-stage infection, thereby ensuring the enhanced safety of the proposed approach and we have demonstrated the potential for cross-species protection between rodent and human *Plasmodium* species.

We further propose that such cross-species protection can be enhanced by the genetic engineering of rodent *Plasmodium* organisms, to express antigens of their human-infective counterparts. We used a transgenic *P. berghei* parasite where the endogenous CS has been replaced by that of *P. falciparum* ($PbCS_{Pf}$) [11] to demonstrate that genetically engineered rodent *Plasmodium* organisms are able to elicit a specific immune response capable of binding and inhibit infection by *P. falciparum*. These results compound a new paradigm in malaria vaccination strategies with optimal immunogenic properties.

SUMMARY OF THE INVENTION

The present invention proposes an alternative strategy for the development of a pre-erythrocytic, whole organism vaccine against malaria, based on the use of rodent parasites as primary immunizing vectors. Rodent *Plasmodium* organisms can be used to induce an immune response in human hosts capable of protecting against infection with human-infective *Plasmodium* spp., by exploiting the cross-species protection potential created by homologous molecules of the rodent parasite. Furthermore, the immunizing potential of these rodent *Plasmodium* organisms can be enhanced by introducing selected immunogenic antigens through genetic engineering. In this strategy, rodent *Plasmodium* organisms can carry antigens of human-infective *Plasmodium* spp. to elicit a specific protective immune response against human

*Plasmodium* parasites, in addition to their natural cross-species protective capability, provided by evolutionarily conserved molecules.

The present invention describes a live rodent *Plasmodium* organism for use against human malaria.

A preferred embodiment of the present invention provides the live rodent *Plasmodium* organism genetically engineered to express genes or gene sections of one or more species of human *Plasmodium* parasites, for use as immunospecific single- or multi-stage immunoeffectors against human malaria.

In another embodiment of the present invention, the previous live rodent *Plasmodium* organism is any member of the protozoan genus *Plasmodium* whose natural host is a rodent, including *P. berghei, P. yoeli, P. vinckei* and *P. chabaudi.*

A preferred embodiment of the present invention provides the use of the live rodent *Plasmodium* organism, wherein the single or multistage immunoeffectors are liver-stage antigens such as circumsporozoite protein (CS), liver stage antigen 1 (LSA-1), thrombospondin-related adhesion protein (TRAP), and liver stage antigen 3 (LSA-3) or blood-stage antigens such as erythrocyte-binding antigen-175 (EBA-175), apical membrane antigen-1 (AMA-I), merozoite surface protein 1 (MSP-1), Duffy-binding protein (DBP), and reticulocyte-binding proteins (RBPs), or gametocyte-specific antigens such as p48/45, or other immunogenic antigens.

In another embodiment of the present invention, the human malaria is caused by any of the human *Plasmodium* parasite from the protozoan genus *Plasmodium* including *P. falciparum, P. vivax, P. malariae, P. ovale* and *P. knowlesi.*

A preferred embodiment of the present invention provides the use of the live rodent *Plasmodium* organism, for the manufacture of an admixture with a pharmaceutically acceptable carrier.

In another embodiment of the present invention, the live rodent *Plasmodium* organism is used for the manufacture of a vaccine against malaria.

DESCRIPTION OF THE DRAWINGS

The following figures provide preferred embodiments for illustrating the description and should not be seen as limiting the scope of invention.

FIG. 1. Rodent *Plasmodium* Parasites Infection and Development Within Human Hepatic Cells.

A) In vitro. Representative pictures of Pb(WT) parasites developing 48 hours post infection in human hepatoma cell lines (Huh-7 and HepG2) and human immortalized hepatocytes (HC-04); B) Ex vivo development. Representative pictures of Pb(WT) parasites developing 48 hours post infection (upper panels) and 72 hours post infection (lower panels) in micro patterned co-cultures of human primary hepatocytes (scale indicates 10 μm). C) Development of exo-erythrocytic forms of Pb(WT) parasites in Huh-7 and HepG2 hepatoma cell lines and HC-04 immortalized human hepatocytes 48 hours post infection as quantified by area measurement (line indicates mean of area and bars represent the 90 and 10 percentile); D) Number of exo-erythrocytic forms developing in Huh-7 and HepG2 hepatoma cells and HC-04 hepatocytes 48 hours post infection with 10000 sporozoites, presented as a % of the number of exo-erythrocytic forms after normalization for cell confluence (bars indicate standard deviation); E) Relative proportion of exo-erythrocytic forms from Pb(WT) parasites developing inside mouse (black bar) and human engraphed hepatocytes (grey bar) in the livers of FRG humanized mice 48 hours post infection; F) Development of exo-erythrocytic forms of Pb(WT) parasites inside mouse hepatocytes (black bars) or human hepatocytes (grey bars) in the FRG humanized mice at 48 hours post infection, as quantified by area measurement (line indicates mean of area and bars represent the 90 and 10 percentile); G) Pictures and projections of parasites developing 48 hours post-infection inside human hepatocytes of liver-humanized mice. Note that the *P. berghei* parasite (red) is clearly within a human, fumarylacetoacetate hydrolase-stained, hepatocyte (white). Scale bars correspond to 10 μm.

FIGS. 2*a* and 2*b*. Rodent *Plasmodium* Parasites Infection of Human Erythrocytes In Vivo.

A1, A2 and A3) Representative flow cytometry plots of measurements of parasitemia in the peripheral blood of chimeric and non-chimeric mice engraphed with human erythrocytes. Simultaneous staining with SYTO-16 for nucleic acids (x-axis) and TER-119 mAB for murine erythroid lineage (y axis) allows the distinction between human and mouse erythrocytes, as well as between infected and non-infected erythrocytes. Using this strategy, it is possible to identify human erythrocytes infected with *P. berghei* parasites as they are expected to fall in the same gate as a positive control of infected human erythrocytes with *P. falciparum*. (mE: murine erythrocytes; hE: human erythrocytes; imE: infected murine erythrocytes; ihE: infected human erythrocytes; bimE: background for infected murine erythrocytes; bihE: background for infected human erythrocytes, A1) Chimeric mice engraphed with human erythrocytes infected with *P. falciparum*; A2) non-chimeric mice infected with *P. berghei*; A3) Chimeric mice engraphed with human erythrocytes infected with *P. berghei*; B1, B2 and B3) Average percentage of infected erythrocytes from either human or murine origin, in chimeric and non-chimeric mice infected with Pb(WT) or *P. falciparum*, across time; B1) Average percentage of infected human erythrocytes (full line) as well as signal background obtained on the expected region for infected mouse erythrocytes (small dotted line) in chimeric mice engraphed with human erythrocytes infected with *P. falciparum*. B2) Average percentage of infected mouse erythrocytes (long dotted line) as well as signal background obtained on the expected region for infected human erythrocytes (small dotted line) in non-chimeric mice infected with *P. berghei*; B3) Average percentage of infected human erythrocytes (full line) as well as average percentage of infected mouse erythrocytes (long dotted line) in chimeric mice engraphed with human erythrocytes infected with *P. berghei*; C1 and C2) Erythrocyte populations obtained after magnetic separation of imE and ihE from chimeric mice engraphed with human erythrocytes infected with *P. berghei*. C1) Representative flow cytometry plot of magnetically separated *P. berghei* infected human erythrocytes present in the peripheral blood of chimeric mice engraphed with human erythrocytes. C2) Representative flow cytometry plot of magnetically separated *P. berghei* infected mouse erythrocytes present in the peripheral blood of chimeric mice engraphed with human erythrocytes; D1 and D2) Cultivation of erythrocyte populations obtained after magnetic separation of imE and ihE from chimeric mice engraphed with human erythrocytes infected with *P. berghei*. D1) Representative pictures of *P. berghei* parasites over-time in culture within human erythrocytes; D2) Representative pictures of *P. berghei* parasites over-time in culture within mouse erythrocytes; Note that *P. berghei* parasites in ihE obtained immediately after magnetic separation only show picnotic forms that eventually degenerate after 20 h in culture, while P. berghei-imE are already mature at the moment of separation and proceed towards complete trophozoite segmentation over time in culture. E) Representative pictures obtained by light and immunofluorescence microscopy observation of blood smears from infected chimeric mice showing multiple P. berghei-infected murine erythrocytes and abnormal, picnotic P. berghei-infected human erythrocytes in the same mice.

Figure 3:
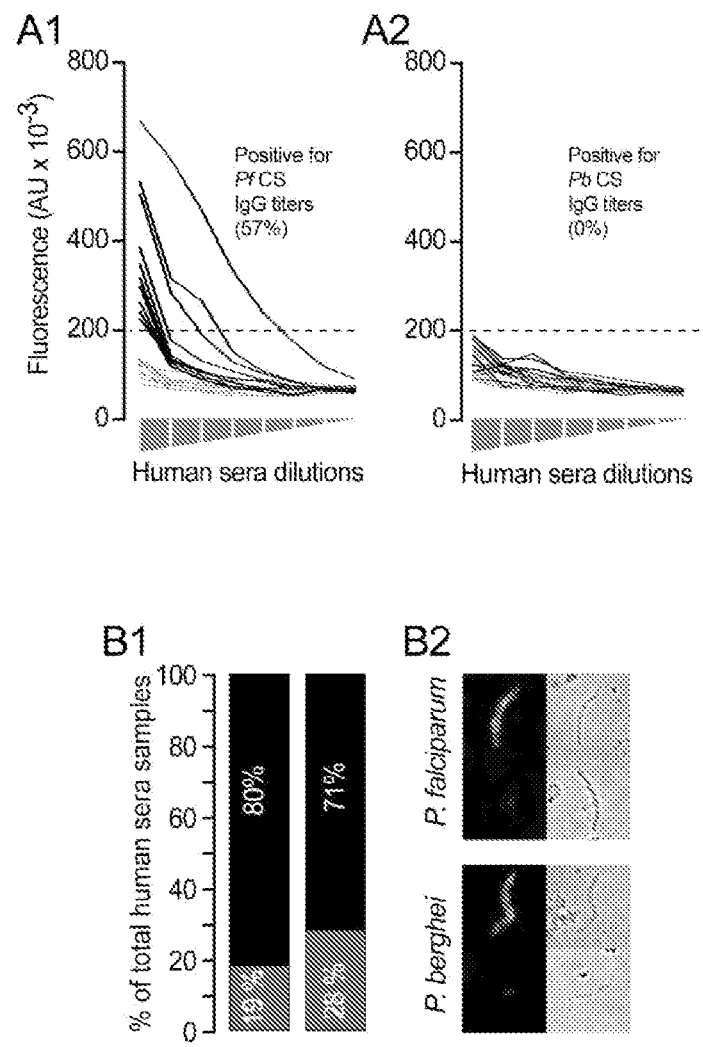

FIG. 3. Rodent *Plasmodium* Parasites Interspecies Cross-Protection.

A1 and A2) CS-specific antibody titers in sera from human malaria patients (n=21); Black represent serum samples positive for P. falciparum CS; A1) P. falciparum CS-specific IgG titers; A2) P. berghei CS-specific IgG titers Black represent serum samples positive for P. falciparum CS; B1 and B2) Recognition and binding of sera from human malaria patients to P. falciparum and P. berghei sporozoites; B1) Proportion of human serum samples recognizing and binding to P. falciparum (right) and P. berghei sporozoites (left); Proportion binding to sporozoites (black) proportion not binding to sporozoites (grey); B2) Representative images of P. falciparum sporozoites binding assays (top) and of P. berghei sporozoites binding assays (bottom).

Figure 4:
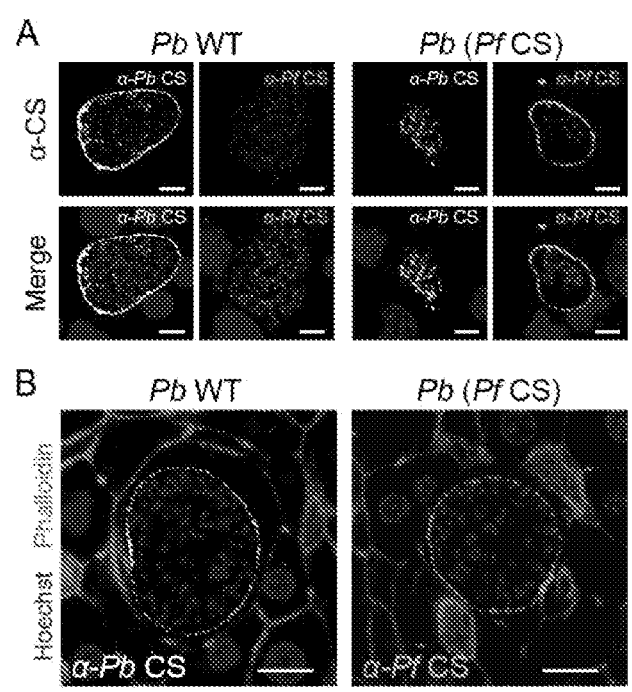

FIG. 4. Genetically Modified Rodent *Plasmodium* Parasites Expressing Human *Plasmodium* Parasite Antigens.

A) Ex vivo. Immunofluorescence microscopy of liver rodent *Plasmodium* parasite forms 48 hours after sporozoites infection of rodent primary hepatocytes; B) In vivo. Immunofluorescence microscopy 45 hours after in vivo sporozoites infection of C57BL/6 rodent malaria models. Note the presence of P. falciparum CS protein (green) in Pb(PfCS) parasites.

Figure 5:
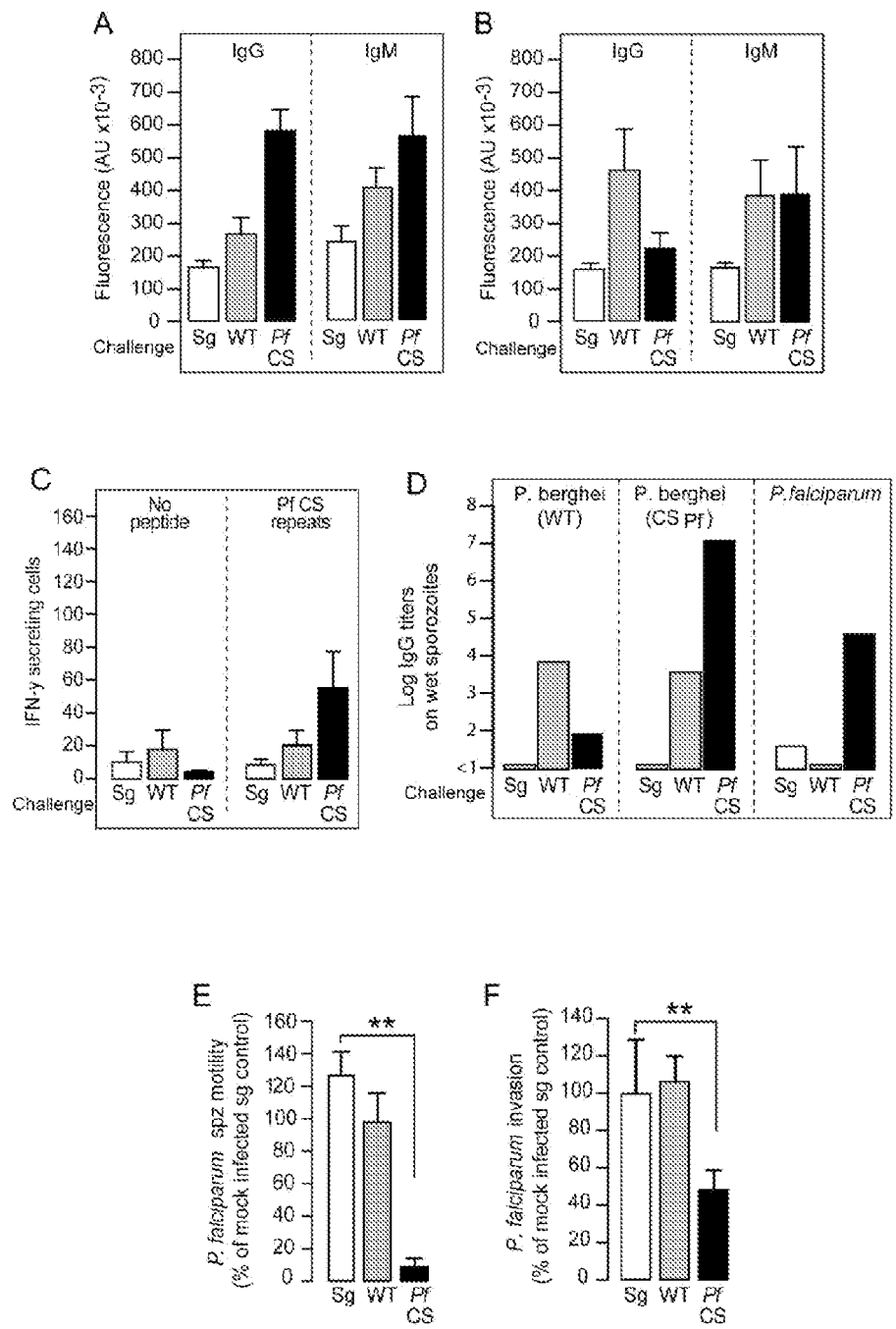

FIG. 5. Immunogenicity of Genetically Modified Rodent *Plasmodium* Parasites.

A and B) Serum samples from mice infected with sporozoites from the different parasite lines were analyzed by ELISA to assay IgG and IgM responses induced against the circumsporozoite protein (CS) in mice challenged with either mock infected salivary-gland injected mice (SG) or mice infected with wild-type *P. berghei* (WT) or the genetically modified $PbCS_{Pf}$ (PfCS); Titers are expressed in arbitrary units of fluorescence (AU) as the highest dilution of sera tested that gave a positive staining; A) IgG and IgM responses induced against *P. falciparum*-CS; B) IgG and IgM responses induced against *P. berghei*-CS; C) ELISPOT analysis of CS-specific T-cell responses in mice challenged with either mock infected salivary-gland injected mice (SG) or mice infected with wild-type *P. berghei* (WT) or the genetically modified $PbCS_{Pf}$ (PfCS); the number of IFN-γ secreting cells in 10^6 splenocytes is presented; D) Binding affinity of immune sera from mice challenged with either mock infected salivary-gland injected mice (SG) or mice infected with wild-type *P. berghei* (WT) or the genetically modified $PbCS_{Pf}$ (PfCS) to wild-type *P. berghei* sporozoites, or genetically modified $PbCS_{Pf}$ or *P. falciparum* sporozoites; E) Gliding motility inhibition assays of *P. falciparum* sporozoites in the presence of sera from mice challenged with either mock infected salivary-gland injected mice (SG) or mice infected with wild-type *P. berghei* (WT) or the genetically modified $PbCS_{Pf}$ (PfCS); F) Hepatic infectivity inhibition assays of *P. falciparum* in the presence of sera from mice challenged with either mock infected salivary-gland injected mice (SG) or mice infected with wild-type *P. berghei* (WT) or the genetically modified $PbCS_{Pf}$ (PfCS).

DETAILED DESCRIPTION OF THE INVENTION

The present invention relates to an alternative approach to malaria vaccination that combines unprecedented versatility with high efficacy, whilst ensuring complete safety. We have demonstrated that (i) rodent malaria sporozoites (spz) can be used as a whole-organism pre-erythrocytic vaccine capable of generating a strong immune response because they are able to successfully infect and develop in human liver cells; (ii) rodent malaria parasites are an extremely safe antigen delivery platform because they are completely unable to complete their life cycle inside human erythrocytes, which renders then unable to cause a disease-triggering human blood-stage infection; (iii) rodent malaria parasites can induce a high level of cross-species protection against human *Plasmodium* species because they possess conserved molecules that can be recognized by the human immune system iv) Genetically engineered rodent *Plasmodium* parasites are highly immunogenic, being able to trigger specific immune responses against an engineered human *Plasmodium* antigen capable of recognizing human *Plasmodium* parasites and inhibiting human *Plasmodium* infection. By rodent *Plasmodium* organism or rodent *Plasmodium* parasite is meant any member of the protozoan genus *Plasmodium* whose natural host is a rodent, including the four known species, *P. berghei, P. yoelii, P. vinckei* and *P. chabaudi*. By human *Plasmodium* organism or human *Plasmodium* parasite is meant any member of the protozoan genus *Plasmodium* known to cause human malaria, including *P. falciparum, P. vivax, P. malariae, P. ovale* and *P. knowlesi*.

(i) Rodent *Plasmodium* Parasites Infect Human Hepatocytes In Vivo

We monitored in parallel the in vitro infection of one mouse and two human hepatoma cell lines (Hepa 1-6, HepG2 and Huh7), and one human immortalized hepatocyte line (HC04), and the ex vivo infection of mouse primary hepatocytes and human primary hepatocyte/fibroblast co-cultures by wild-type *P. berghei*, a rodent *Plasmodium* organism. Infection assessments by quantitative real-time PCR (qRT-PCR) and fluorescence microscopy showed that *P. berghei* traverses, invades and develops to similar extents in all in vitro systems studied and that it is able to invade and develop inside rodent and human primary hepatic cells ex vivo (FIG. 1A,B,C,D).

In order to ascertain whether *P. berghei* is able to infect human liver cells in an in vivo context, we injected sporozoites into liver-humanized mice ($^{LH}$mice) and monitored hepatic infection by confocal fluorescence microscopy. Our results show that *P. berghei* can effectively infect human hepatocytes engrafted in the livers of the chimeric $^{LH}$mice. A comparison between infection of the human and mouse hepatocytes in the chimeric livers, reveals that the parasite is capable of similar development inside either type of cell (FIG. 1E-G).

Additionally, we employed a genetically engineered rodent *P. berghei* parasite where the endogenous CS has been replaced by that of *P. falciparum* ($PbCS_{Pf}$) [11]. We evaluated the hepatic infection behavior of this genetically modified parasite and showed that it retains the ability to infect human hepatic cells in vitro, as well primary hepatocytes as well as the livers of $^{LH}$mice.

Overall, these results show that the rodent *P. berghei* parasite is fully competent to infect human hepatocytes, and that this competence is retained in the genetically engineered $PbCS_{Pf}$ parasite, thereby fulfilling the immunity-generation condition for a malaria vaccine.

(ii) Rodent *Plasmodium* Parasites are Unable to Cause a Human Blood-Stage Infection that Leads to Pathology In order to be safe, a rodent *Plasmodium* organism-based malaria vaccine must ensure that the immunizing parasite is unable to cause disease in humans. This requires that rodent

Figure 2A:
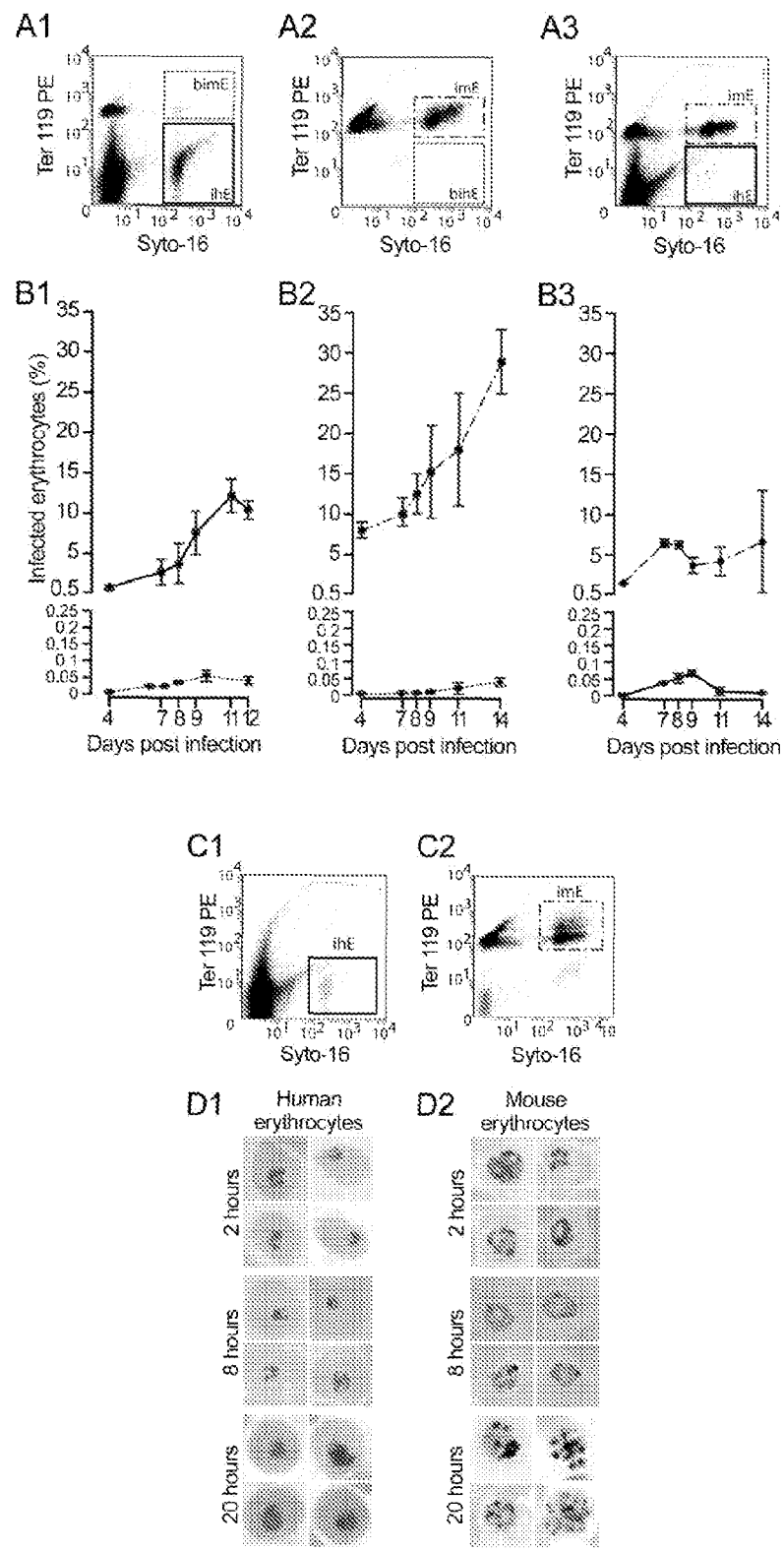
Figure 2B:
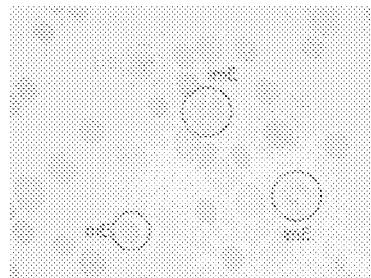
Figure 2B:
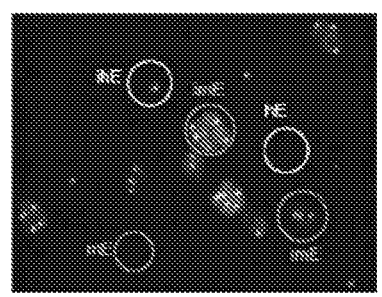
Figure 2B:
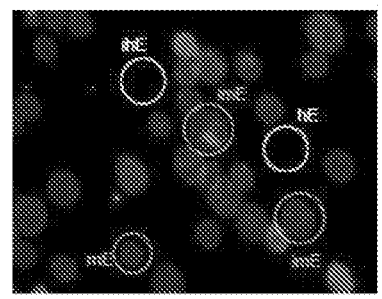

*Plasmodium* merozoites are unable to effectively invade and multiply inside human red blood cells (RBC. In order to ascertain this, we employed a strategy based on the use of blood-humanized mice ($^{BH}$mice), engrafted with defined proportions of human erythrocytes, which have been developed as models to evaluate drug efficacy against *P. falciparum* infection[12]. This system can be coupled with the use of the nuclear SYTO-16 and the mouse-specific TER-119 dyes to distinguish infected from non-infected cells and human from rodent erythrocytes, respectively, and thereby monitor infection of either type of cell by flow cytometry (FIG. 2A1, 2A2, 2A3).

We started by infecting $^{BH}$mice bearing different degrees of chimerism by transfusion of *P. berghei*-infected mouse blood and monitored the parasitemia in these mice at regular intervals, using non-chimeric mice as controls. Our results show that while the SYTO-16$^+$/TER-116$^+$ population increased to values ~5%, showing, as expected, infection of the mouse RBC ($^m$RBC) population, the SYTO-16$^+$/TER-116$^-$ population that would correspond to infected human RBCs ($^h$RBCs) never surpassed 0.2%, remaining within the range of the background levels observed for the non-humanized mice (FIG. 2A1, 2A2, 2A3, 2B1, 2B2, 2B3).

This result suggested that *P. berghei* is unable to infect $^h$RBCs or that it may do so at very low levels. It is worth noting that this occurs in the context of a chimeric mouse, which contains a significant population of $^m$RBCs that serve as an effective reservoir for the production of large numbers of merozoites. To further investigate the possibility of human RBC infection under these conditions, we analysed blood samples from these mice after staining with the nuclear dye DAPI and with TER-116. We found very rare instances of DAPI$^+$/TER-116$^-$ cells, which indicated that a small degree of invasion of $^h$RBCs could indeed occur. However, we were unable to find any $^h$RBC bearing more than a single parasite nucleus, suggesting that *P. berghei* is unable to replicate inside the few $^h$RBCs that it may invade (FIG. 2E).

Crucially, in vitro cultivation of flow cytometry-isolated infected $^h$RBCs showed that these parasites are indeed incapable of completing their intra-erythrocytic life cycle in $^h$RBCs (FIG. 2C1, 2C2, 2D1, 2D2), rendering them safe for use in humans. Similar results were obtained when infection was carried out with the PbCS$_{Pf}$ parasite.

Since in these experiments infection was initiated with second-generation merozoites, obtained by transfusion of infected RBCs, we decided to investigate the behavior of the first-generation merozoites that are produced in the liver. To do this, we infected $^{BH}$mice with sporozoites collected from the salivary glands of *P. berghei*- or PbCS$_{Pf}$-infected mosquitoes and, using non-chimeric mice as controls, we carried out the same type of analysis as described above. Our results show that merozoites produced in the liver behave similarly to second-generation merozoites, showing that rodent *P. berghei* parasites are safe for use in humans and do not present the risks associated with inefficient attenuation of *P. falciparum* sporozoites.

(iii) Rodent *Plasmodium* Parasites have a High Cross-Species Protection Potential Against Human *Plasmodium* Parasites We evaluated serum samples from African malaria-infected individuals from Cameroon and Tanzania for the presence of antibodies against the *P. berghei* and *P. falciparum* CS proteins and for their ability to recognize spz from both these species. Our results showed that while none of these samples contained antibodies against *P. berghei* CS (FIG. 3A1, 3A2), 71% of them were able to recognize both *P. falciparum* and *P. berghei* spz (FIG. 3B1, 3B2). These data show that naturally acquired immunity against malaria includes an antibody response against conserved human *Plasmodium* parasites and rodent *plasmodium* parasites epitopes on spz, besides the CS protein. Overall, these results demonstrate that the use of rodent *Plasmodium* parasites as a vaccination platform has the potential to raise an immune response against currently unknown conserved antigens.

(iv) Immunization with Genetically Modified Rodent *Plasmodium* Parasites Elicits Specific Highly Effective Protection Against Human *Plasmodium* Infection An additional advantage of our proposed vaccination method relies on the notion that we can enhance the intrinsic cross-species protection provided by rodent *Plasmodium* parasites by introducing antigens of human *Plasmodium* parasites through genetic modification, which will elicit highly effective specific immune responses.

To establish the proof-of-concept of our proposed strategy, we employed the rodent PbCS$_{Pf}$ parasite. We used immunofluorescence microscopy to confirm that PbCS$_{Pf}$ expresses *P. falciparum* CS in liver cells, either ex vivo (FIG. 4A) or in vivo. (FIG. 4B). We then evaluated the immunogenicity of these transgenic parasites in rodent models of infection and determined the specificity of this response for the engineered *P. falciparum* CS antigen. C57BL/6 mice were infected with PbCS$_{Pf}$ sporozoites and subsequently treated with chloroquine to prevent the development of blood parasitemia and disease. Five days after the initiation of chloroquine treatment, the mice were sacrificed and immune serum was obtained from collected blood. Pre-immune serum from uninfected mice and serum from mice immunized with wild-type *P. berghei* were obtained and used as controls in these experiments. Antibodies against *P. falciparum* CS in the serum were quantified by ELISA (FIG. 5A, 5B). Our results show that mice immunized with the PbCS$_{Pf}$ parasite produced significant amounts of this antibody, showing that immunization of rodents with PbCS$_{Pf}$ elicited the generation of antibodies directed against *P. falciparum* CS, which are known to mediate protection against the human-infective parasite [13].

Moreover, we demonstrated a clear cellular immune response against *P. falciparum* CS epitopes (FIG. 5C). Finally, we showed that the serum of mice immunized with the genetically modified rodent PbCS$_{Pf}$ can recognize and bind with high avidity to human *Plasmodium* sporozoites (FIG. 5D). Moreover, we showed that this immune serum is able to functionally inhibit the gliding motility (FIG. 5E) and hepatic cell invasion (FIG. 5F) of human *Plasmodium* parasites.

Overall, our data show that the genetic modification of rodent *Plasmodium* parasites can substantially increase the immunizing potential of these parasites against human *Plasmodium* parasites.

CONCLUSIONS

Whole-organism approaches such as those provided by radiation attenuated (RAS) and genetically attenuated (GAS) sporozoites appear as very attractive alternatives to subunit-based pre-erythrocytic vaccination strategies, despite considerable technological challenges in terms of manufacturing, formulation, and delivery of such attenuated sporozoite vaccines. However, both these approaches pose undeniable safety concerns that arise from the fact that they are based on the attenuation of *P. falciparum*, the most deadly human malaria parasite.

We propose an alternative strategy for the development of a pre-erythrocytic, whole-organism vaccine against malaria, based on the cross-species protection potential between rodent and human *Plasmodium* parasites. Such a vaccine may elicit cross-species protection by rodent antigens that may be immunogenic against their human *Plasmodium* spp. counterparts. Examples of cross-species protection induced by components other than CS following immunization with irradiated malaria sporozoites are available. This might be the case, for instance, of CelTOS, for cell-traversal protein for ookinetes and sporozoites, which has been recently identified as a target antigen for a pre-erythrocytic vaccine, based on its ability to induce protective immunity through humoral and cellular immune responses. CelTOS is highly conserved among the *Plasmodium* species and immunization with pre-erythrocytic antigen CelTOS from *P. falciparum* has been shown to elicit cross-species protection against a heterologous challenge with *P. berghei*, suggesting that the reverse effect might also take place.

Besides their cross-protective potential, the immunogenicity of rodent *Plasmodium* parasites can be enhanced by genetic engineering, effectively turning them into platforms for the delivery of immunogenic antigens of human-infective *Plasmodium* species, capable of eliciting highly efficient specific immune responses. Of course more than one antigen, already known or hitherto unknown, can be introduced, for either single or multiple stages of the *Plasmodium* life cycle, and for a single or multiple species of human *Plasmodium* organisms, because such redundancy may ensure an additional degree of protection against infection of parasitemia.

In this invention, we demonstrate that the rodent parasite *P. berghei* can infect human hepatocytes whilst being unable to cause a human blood stage infection. These constitute two of the essential premises for a rodent-based parasite to be evaluated as a vaccination strategy. The third one is that a transgenic rodent *Plasmodium* parasite may elicit a response against a challenge with a human-infective *Plasmodium* species. To demonstrate this assumption, we employed a *P. falciparum* CS-expressing mutant of *P. berghei* ($PbCS_{Pf}$) and showed that it retains the main features of its wild-type counterpart whilst eliciting a specific protective response against a *P. falciparum* challenge. This establishes the proof-of-principle of our proposed strategy and opens further avenues for the design and production of other vaccine candidates based on the same principle.

PbCSPf itself has the drawback that it produces relatively low numbers of salivary gland sporozoites and lower hepatic infectivity than wild-type *P. berghei*. This is most likely due to the absence of the endogenous CS, coupled with an inappropriate conformation of the *P. falciparum* protein in this parasite. Thus, several alternatives may be envisaged in order to improve the infection yields of PbCSPf, such as the heterologous expression of *P. falciparum* CS in a neutral locus, under the control of the endogenous CS promoter, in addition rather than as a replacement of the endogenous protein.

The use of rodent parasites as "piggy-backs" for human malaria genes can be extended to include antigens other than CS. Among the obvious candidates, to generate a pre-erythrocytic immune response, are the thrombospondin-related adhesion protein (TRAP) and liver stage antigen 1 (LSA-1), both of which are expected to present immunogenic potential.

In addition, sterile protective immunity against malaria is directed against a panel of novel *P. falciparum* antigens rather than one antigen in isolation. Or strategy also allows for the inclusion of blood-stage antigens. Apical membrane antigen I (AMA-I), erythrocyte-binding antigen-175 (EBA-175), and merozoite surface protein 1 (MSP-1) are prime candidates among these, given their established or proposed immunogenicity. When placed under the control of promoters, that enable their expression during the liver stages of infection, these antigens are expected to prime the host's immune system against *P. falciparum* blood-stages, creating an additional layer of protection. Moreover, this approach can be used to introduce a transmission blocking component in the pseudo-attenuated vaccine, by engineering gametocyte-specific genes, such as p48/45, into the rodent *Plasmodium* platform.

This strategy can be extended beyond the development of immunity against *P. falciparum*, as one may envisage the inclusion of *P. vivax* antigens, such as CS, orthologs of the *P. falciparum* genes listed above, Duffy-binding protein (DBP), or reticulocyte-binding proteins (RBPs), in the immunogenic platform.

REFERENCES

1. Hill A V. Vaccines against malaria. Philos Trans R Soc Lond B Biol Sci 2011; 366:2806-14.
2. Agnandji S T, Lell B, Soulanoudjingar S S, et al. First results of phase 3 trial of RTS,S/AS01 malaria vaccine in African children. N Engl J Med 2011; 365:1863-75.
3. Prudencio M, Rodriguez A and Mota M M. The silent path to thousands of merozoites: the *Plasmodium* liver stage. Nat Rev Microbiol 2006; 4:849-56.
4. Clyde D F, McCarthy V C, Miller R M and Hornick R B. Specificity of protection of man immunized against sporozoite-induced *falciparum* malaria. Am J Med Sci 1973; 266:398-403.
5. Mueller A K, Labaied M, Kappe S H and Matuschewski K. Genetically modified *Plasmodium* parasites as a protective experimental malaria vaccine. Nature 2005; 433: 164-7.
6. Butler N S, Schmidt N W, Vaughan A M, Aly A S, Kappe S H and Harty J T. Superior antimalarial immunity after vaccination with late liver stage-arresting genetically attenuated parasites. Cell Host Microbe 2011; 9:451-62.
7. Kumar K A, Sano G, Boscardin S, et al. The circumsporozoite protein is an immunodominant protective antigen in irradiated sporozoites. Nature 2006; 444:937-40.
8. Mauduit M, Gruner A C, Tewari R, et al. A role for immune responses against non-CS components in the cross-species protection induced by immunization with irradiated malaria sporozoites. PLoS One 2009; 4:e7717.
9. Gruner A C, Mauduit M, Tewari R, et al. Sterile protection against malaria is independent of immune responses to the circumsporozoite protein. PLoS One 2007; 2:e1371.
10. Annoura T, Ploemen I H, van Schaijk B C, et al. Assessing the adequacy of attenuation of genetically modified malaria parasite vaccine candidates. Vaccine 2012.
11. Tewari R, Spaccapelo R, Bistoni F, Holder A A and Crisanti A. Function of region I and II adhesive motifs of *Plasmodium falciparum* circumsporozoite protein in sporozoite motility and infectivity. J Biol Chem 2002; 277:47613-8.
12. Jimenez-Diaz M B, Mulet T, Viera S, et al. Improved murine model of malaria using *Plasmodium falciparum* competent strains and non-myelodepleted NOD-scid IL2Rgammanull mice engrafted with human erythrocytes. Antimicrob Agents Chemother 2009; 53:4533-6.

13. Schwenk R J, Richie T L. Protective immunity to pre-erythrocytic stage malaria. Trends Parasitol 2011; 27:306-14.

The invention claimed is:

1. A method for inducing an immune response against a human malaria parasite,
wherein said method comprises administering to a human subject an effective amount of live *Plasmodium berghei* sporozoites, wherein said *Plasmodium berghei* is genetically engineered to express a circumsporozoite protein (CS), or an antigenic fragment thereof, of a human malaria parasite.

2. The method of claim 1, wherein said *Plasmodium berghei* is genetically engineered to express a second protein, or antigenic fragment thereof, of a human malaria parasite.

3. The method of claim 1, wherein said human malaria parasite is selected from the group consisting of *Plasmodium falciparum, Plasmodium vivax, Plasmodium malariae, Plasmodium ovale* and *Plasmodium knowlesi*.

4. A method for vaccinating against a human malaria parasite,
wherein said method comprises administering to a human subject an effective amount of live *Plasmodium berghei* sporozoites, wherein said *Plasmodium berghei* is genetically engineered to express a circumsporozoite protein (CS), or an antigenic fragment thereof, of a human malaria parasite.

5. The method of claim 4, wherein said human malaria parasite is selected from the group consisting of *Plasmodium falciparum, Plasmodium vivax, Plasmodium malariae, Plasmodium ovale* and *Plasmodium knowlesi*.

6. The method of claim 4, wherein said *Plasmodium berghei* is genetically engineered to express a second protein, or antigenic fragment thereof, of a human malaria parasite.

7. The method of claim 2, wherein said second protein is selected from the group consisting of: liver stage antigen 1 (LSA-1), thrombospondin-related adhesion protein (TRAP), liver stage antigen 3 (LSA-3), erythrocyte-binding antigen-175(EBA-175), apical membrane antigen-1 (AMA-I), merozoite surface protein 1 (MSP-1), Duffy-binding protein (DBP), and p48/45.

8. The method of claim 6, wherein said second protein is selected from the group consisting of: liver stage antigen 1 (LSA-1), thrombospondin-related adhesion protein (TRAP), liver stage antigen 3 (LSA-3), erythrocyte-binding antigen-175 (EBA-175), apical membrane antigen-1 (AMA-I), merozoite surface protein 1 (MSP-1), Duffy-binding protein (DBP), and p48/45.

* * * * *